US010860732B2

(12) United States Patent
Guirguis et al.

(10) Patent No.: US 10,860,732 B2
(45) **Date of Patent: *Dec. 8, 2020**

(54) SYSTEM AND METHOD FOR REAL-TIME TRANSACTIONAL DATA OBFUSCATION

(71) Applicant: ORACLE INTERNATIONAL CORPORATION, Redwood Shores, CA (US)

(72) Inventors: Shenoda Guirguis, Pittsburgh, PA (US); Alok Pareek, Hillsborough, CA (US); Stephen Wilkes, Santa Clara, CA (US)

(73) Assignee: ORACLE INTERNATIONAL CORPORATION, Redwood Shores, CA (US)

( * ) Notice: Subject to any disclaimer, the term of this patent is extended or adjusted under 35 U.S.C. 154(b) by 664 days.

This patent is subject to a terminal disclaimer.

(21) Appl. No.: 14/925,870

(22) Filed: Oct. 28, 2015

(65) Prior Publication Data

US 2016/0085982 A1 Mar. 24, 2016

Related U.S. Application Data

(63) Continuation of application No. 13/077,800, filed on Mar. 31, 2011, now Pat. No. 9,298,878.

(Continued)

(51) Int. Cl.
*G06F 7/00* (2006.01)
*G06F 21/62* (2013.01)

(Continued)

(52) U.S. Cl.
CPC .......... *G06F 21/6209* (2013.01); *G06F 9/466* (2013.01); *G06F 16/2379* (2019.01);

(Continued)

(58) Field of Classification Search
CPC ...................................................... G06F 16/29

(Continued)

(56) References Cited

U.S. PATENT DOCUMENTS 6,016,501 A 1/2000 Martin et al.
6,173,388 B1 * 1/2001 Abercrombie ...... G06F 9/30145 345/563

(Continued)

FOREIGN PATENT DOCUMENTS

CN 101615199 12/2009
CN 101719165 6/2010

(Continued)

OTHER PUBLICATIONS

Shenoda Guirguis et al., "Bronzegate: Real-Time Transactional Data Obfuscation for Goldengate", Jan. 2010, 6 Pages.

(Continued)

*Primary Examiner* — Eliyah S. Harper
(74) *Attorney, Agent, or Firm* — Tucker Ellis LLP

(57) ABSTRACT

A system and method for providing transactional data privacy while maintaining data usability, including the use of different obfuscation functions for different data types to securely obfuscate the data, in real-time, while maintaining its statistical characteristics. In accordance with an embodiment, the system comprises an obfuscation process that captures data while it is being received in the form of data changes at a first or source system, selects one or more obfuscation techniques to be used with the data according to the type of data captured, and obfuscates the data, using the selected one or more obfuscation techniques, to create an obfuscated data, for use in generating a trail file containing the obfuscated data, or applying the data changes to a target or second system.

20 Claims, 8 Drawing Sheets

116
Original/
Source DB
Capture
118
Trail
120
histogram 1
122
Parameter File
108
UserExit
Process
104
histogram 2
124
Dictionary1:
names
110
Dictionary2:
addresses
112
102

Related U.S. Application Data

(60) Provisional application No. 61/369,000, filed on Jul. 29, 2010.

(51) Int. Cl.
*G06F 16/28* (2019.01)
*G06F 16/23* (2019.01)
*G16H 10/60* (2018.01)
*G06F 9/46* (2006.01)
*G06F 17/30* (2006.01)
*G06F 16/31* (2019.01)
*G06F 16/29* (2019.01)

(52) U.S. Cl.
CPC ...... *G06F 16/283* (2019.01); *G06F 17/30377* (2013.01); *G06F 17/30592* (2013.01); *G06F 21/6254* (2013.01); *G16H 10/60* (2018.01); *G06F 16/29* (2019.01); *G06F 16/313* (2019.01); *G06F 17/30616* (2013.01)

(58) Field of Classification Search
USPC .......................................................... 707/769
See application file for complete search history.

(56) References Cited

U.S. PATENT DOCUMENTS 6,212,628 B1* 4/2001 Abercrombie ...... G06F 9/30014 712/16
6,687,848 B1 2/2004 Najmi
6,753,889 B1 6/2004 Najmi
6,877,023 B1 4/2005 Maffeis
7,031,987 B2 4/2006 Mukkamalla
7,039,773 B2 5/2006 Hu
7,076,508 B2 7/2006 Bourbonnais et al.
7,254,586 B2 8/2007 Chen
7,257,690 B1 8/2007 Baird
7,299,230 B2 11/2007 Liou
7,310,716 B2 12/2007 Galipeau et al.
7,321,939 B1 1/2008 Porter
7,360,111 B2 4/2008 Adya et al.
7,571,173 B2 8/2009 Yang
7,702,698 B1 4/2010 Chakravarthy
7,716,181 B2 5/2010 Todd
7,730,107 B1 6/2010 Shultz
7,873,635 B2 1/2011 Wang
7,885,922 B2 2/2011 Pareek
8,161,468 B2 4/2012 Todd
8,224,834 B2 7/2012 Akaboshi
8,402,358 B2 3/2013 Knauft
8,538,886 B1* 9/2013 Iu ........................... G06T 1/005 380/252
8,666,939 B2 3/2014 O'Krafka
9,130,988 B2* 9/2015 Seifert ................ H04L 63/1416
9,298,878 B2* 3/2016 Guirguis ............ G06F 21/6254
10,331,753 B1* 6/2019 Zhang .................. H04W 4/023
2002/0123987 A1* 9/2002 Cox .................... G06K 9/6282
2002/0169842 A1 11/2002 Christensen
2002/0174340 A1 11/2002 Dick
2004/0148585 A1 7/2004 Sengodan
2004/0254919 A1 12/2004 Giuseppini
2005/0102264 A1 5/2005 Nason
2005/0165858 A1 7/2005 Tom
2005/0253739 A1 11/2005 Hu
2006/0041540 A1 2/2006 Shannon
2006/0212356 A1 9/2006 Lambert
2007/0044069 A1 2/2007 Doucette
2007/0226263 A1 9/2007 Liou
2007/0288458 A1 12/2007 Kacmarcik
2007/0299885 A1 12/2007 Pareek
2008/0077601 A1 3/2008 Liou
2009/0106327 A1 4/2009 Dilman
2009/0313311 A1 12/2009 Hoffmann
2010/0042583 A1 2/2010 Gervais
2010/0191884 A1 7/2010 Holenstein
2010/0205123 A1 8/2010 Sculley
2010/0205151 A1 8/2010 Kuroide
2010/0274768 A1 10/2010 Wang
2010/0274788 A1 10/2010 Coker
2011/0029681 A1 2/2011 Lee
2011/0179011 A1 7/2011 Cardno
2011/0229681 A1 9/2011 Sakamoto
2011/0307524 A1 12/2011 Aitken
2012/0023116 A1 1/2012 Wilkes
2012/0030165 A1 2/2012 Guirguis
2012/0030172 A1 2/2012 Pareek
2012/0137276 A1 5/2012 Todd
2012/0295716 A1 11/2012 Lee
2012/0303559 A1 11/2012 Dolan
2013/0246376 A1 9/2013 Padmanabhan
2014/0172886 A1 6/2014 Wilkes
2014/0280356 A1* 9/2014 Danilak .............. G06F 16/2272 707/796
2016/0055611 A1* 2/2016 Manevitch ............... G06T 1/20 345/501
2016/0379083 A1* 12/2016 Sala ........................ G06K 9/52 345/633

FOREIGN PATENT DOCUMENTS

JP S63-14390 A 1/1988
JP 2000-082070 A 3/2000
JP 2004-341926 A 12/2004
JP 2005293323 10/2005
JP 2007-114817 A 5/2007
WO 2007134250 11/2007

OTHER PUBLICATIONS

Oracle®, Fred Louis, Oracle GoldenGate: Architecture for Real-Time Replication, Jan. 2010, 69 pages.
European Patent Office, International Searching Authority, International Search Report and Written Opinion dated Dec. 13, 2018 for International Application No. PCT/US2018/053441, 10 pages.
European Patent Office, Annex to the European Search Report dated Aug. 21, 2018 for European Patent Application No. 18182168.7, 10 pages.
Imran Chaudhry, "DSE Advanced Replication in DSE 5.1", published Jul. 11, 2017, https://www.datastax.com/dev/blog/advanced-replication-in-dse-5-1, 11 pages.
Novell®, "DirXML 1.0 Administration Guide: Removing the Boundaries for E-Business", Novell, Inc., Nov. 2000, 104 pages.
Oracle®, "Oracle Fusion Middleware: Using Oracle GoldenGate for Big Data", Release 12.3.2.1, May 2018, 335 pages.
Oracle®, Oracle Help Center, "Fusion Middleware Using Oracle GoldenGate for Big Data: 17 Using Oracle GoldenGate Capture for Cassandra", 27 pages.
Vladimir Vajda, "Cassandra to Kafka Data Pipeline (Part 1)", published Aug. 12, 2017, https://dzone.com/articles/cassandra-to-kafka-data-pipeline-part-1, 11 pages.
Vladimir Vajda, "Cassandra to Kafka Data Pipeline (Part 2)", published Nov. 20, 2017, https://dzone.com/articles/cassandra-to-kafka-data-pipeline-part-2, 7 pages.
State Intellectual Property Office of the People's Republic of China, Search Report for Chinese Application No. 201180036429.0, dated Sep. 1, 2015, 2 pages.
Unknown Author, Oracle GoldenGate Administration Guide, Version 10.4, Oct. 2009, pp. 13-16, 333-337, Oracle Internation Corporation. Retrieved on Feb. 17, 2015, from <URL: https://docs.oracle.com/cd/E15881_01/doc.104/gg_wux_admin_v104.pdf>.
Japanese Patent Office, Office Action in connection with Japanese Patent Application No. 2013-521774, dated Mar. 3, 2015, 4 pages.
International Searching Authority at the European Patent Office, International Search Report and Written Opinion for PCT International Patent Application No. PCT/US2011/036508, dated Feb. 18, 2013, 10 pages.
Soorma, GoldenGate Tutorial 1—Concepts and Architecture, Feb. 18, 2010, 4 pages.

(56) References Cited

OTHER PUBLICATIONS

Oracle International Corporation, Oracle GoldenGate Administrative Guide, Version 10.4, Oct. 2009, 343 pages.
Unknown Author, MySQL 5.0 Reference Manual Achieved version from 04.01.2010, Jan. 4, 2010, 3 pages.
Louis, Oracle GoldenGate: Architecture for Real-Time Replication, Jan. 2010, 69 pages.
Unknown Author, Oracle GoldenGate, Oracle Data Sheet, Sep. 2009, 4 pages.
Blyth, Oracle GoldenGate—An Overview, Jul. 2010, 58 pages.
Unknown Author, Oracle Technology Overview, Jun. 2010, 30 pages.
Katsumi Kumakura, "Development of Distributed Database by Way of Replication", SQL Server magazine, Japan, SHOEISHA Co.,Ltd., Feb. 15, 2004, No. 13, pp. 58-66. Partial Translation—English translation of p. 60 only.
United States Patent and Trademark Office, Ex Parte Quayle dated Oct. 18, 2019 for U.S. Appl. No. 15/881,432, 16 pages.
United States Patent and Trademark Office, Notice of Allowance and Fee(S) Due dated July 3, 2020 for U.S. Appl. No. 15/881,432 12 pages.
United States Patent and Trademark Office, Office Action dated June 2, 2020 for U.S. Appl. No. 16/145,707, 16 pages.
European Patent Office, Communication pursuant to Article 94(3) EPC dated Jan. 24, 2020 for European Patent Application No. 18182168.7, 4 pages.

* cited by examiner

```
GT-ANeNDS Algorithm: High Level

Input: dataset specifications (data-type,
histogram, and semantics)

Input: Transactional data item (transaction-
ID,value of data item)

Output: obfuscated value.

BEGIN

   Based on the semantics, determine the
   distance between the origin and the item
   value.

   Based on this distance, histogram and the
   semantics, pick the nearest neighbor.

   Based on semantics, apply the proper GT
   technique to the nearest neighbor.

   Return the obfuscated value.

END
```

```
Special Function 1: Obfuscating identifiable
numerical data
BEGIN
  temp1 ← Apply FaNDS to digits of input.
  temp1 ←Rotation(temp1)
  temp2 ← temp1 + original number.
  temp2← Truncate(temp2,length(input))
  For i=1 to length(input)
     Temp3[i] ← randomly pick between temp1[i]
     and temp2[i] based on input[i].
  Next i
  return Temp3 as the obfuscated data.
END
```

Table 1: Input to Obfuscation Module

| Data-Type | Semantics | Obfuscation Technique |
|---|---|---|
| Numerical | General | GT-ANeNDS<br>GT technique: rotation |
| Numerical | Identifiable (numbers or text) Such as: SSN, Credit Card, driving license number, etc. | Special Function 1 |
| Date | General | No Obfuscation OR Special Function 2. |
| Large Objects | General (Medical Reports, X-Rays, etc.) | No Obfuscation. |
| Boolean | General (s.a.: true/false, gender, etc.) | Randomly set, with certain probability. |
| Text | Identifiable (Such as: Names and contacts.) | Random replacement from a "Dictionary". |
| Text | General | No Obfuscation |
| Any other data type | | GT-ANeNDS if applicable. |

Original Values

| | SSN | First Name | Last Name | DOB | G | Credit Card | Bank Balance |
|---|---|---|---|---|---|---|---|
| 1 | 772877278 | Paul | Dillon | Jul 23, 1980 | M | 0987678543543276 | $4,310.76 |
| 2 | 099099900 | Marty | Allen | Jul 24, 1980 | M | 9020488205617100 | $905.17 |
| 3 | 293487109 | Mary | Marc | Jul 25, 1980 | F | 1234567890123450 | $2,500.03 |
| 4 | 370805980 | Hillary | Clinton | Jul 26, 1980 | F | 4134754103803630 | $270,100.32 |
| 5 | 832875183 | Barak | Obama | Jul 27, 1980 | M | 1903749913701830 | $203,000.76 |

160

Obfuscated Values

| | SSN | First Name | Last Name | DOB | G | Credit Card | Bank Balance |
|---|---|---|---|---|---|---|---|
| 1 | 116698616 | PALMER | ADMON | Dec 23, 1980 | M | 2011116131532110 | $91.00 |
| 2 | 007990774 | WILL | RANDALL | Jan 9, 1920 | M | 1399919063932230 | $671.00 |
| 3 | 724401663 | WILL | GARFIELD | Jan 9, 1971 | M | 0315672200134567 | $1,683.00 |
| 4 | 676277247 | HARLAN | RAJAN | Jan 10, 1971 | F | 1811011171140110 | $317,888.00 |
| 5 | 196990616 | CECILY | ABBA | Jan 11, 1921 | F | 0131211312620111 | $50,816.00 |

SYSTEM AND METHOD FOR REAL-TIME TRANSACTIONAL DATA OBFUSCATION

CLAIM OF PRIORITY

This application is a continuation of U.S. patent application Ser. No. 13/077,800, titled "SYSTEM AND METHOD FOR REAL-TIME TRANSACTIONAL DATA OBFUSCATION', filed on Mar. 31, 2011 and claims the benefit of priority to U.S. Provisional Patent Application No. 61/369,000, titled "SYSTEM AND METHOD FOR REAL-TIME TRANSACTIONAL DATA OBFUSCATION", filed Jul. 29, 2010; which application is herein incorporated by reference.

COPYRIGHT NOTICE

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

FIELD OF INVENTION

The present invention is generally related to computer transactions, and is particularly related to a system and method for providing transactional data privacy while maintaining data usability, including the use of different obfuscation functions for different data types to securely obfuscate the data, in real-time, while maintaining its statistical characteristics.

BACKGROUND

New data privacy laws have appeared recently, such as the HIPAA laws for protecting medical records, and the PCI guidelines for protecting credit card information. Data privacy can be defined as maintaining the privacy of Personal Identifiable Information (PII) from unauthorized accessing. PII includes any piece of data that can be used alone, or in conjunction with additional information, to uniquely identify an individual. Examples of such information include national identification numbers, credit card numbers, as well as financial and medical records. Access control methods and data encryption provide a level of data protection from unauthorized access. However, it is not enough—for example, it does not prohibit identity thefts. It was recently suggested that 70% of data privacy breaches are internal breaches that involve an employee from the enterprise who has access to some training or testing database replica, which contains all the PII. Accordingly, in addition to access control, what are needed are techniques to protect such datasets, including preserving the data usability while protecting its privacy. These challenges are further complicated when realtime requirements are added. This is the general area that embodiments of the invention are intended to address.

SUMMARY

Described herein is a system and method for providing transactional data privacy while maintaining data usability, including the use of different obfuscation functions for different data types to securely obfuscate the data, in real-time, while maintaining its statistical characteristics. In accordance with an embodiment, the system comprises an obfuscation process that captures data while it is being received in the form of data changes at a first or source system, selects one or more obfuscation techniques to be used with the data according to the type of data captured, and obfuscates the data, using the selected one or more obfuscation techniques, to create an obfuscated data, for use in generating a trail file containing the obfuscated data, or applying the data changes to a target or second system.

BRIEF DESCRIPTION OF THE FIGURES

FIG. 2 illustrates the use of a GT-ANeNDS algorithm, in accordance with an embodiment.

FIG. 4 illustrates a function for obfuscating identifiable numerical data, in accordance with an embodiment.

FIG. 5 illustrates a table of possible data-types and semantics, and which technique the system can use to obfuscate each data type, in accordance with an embodiment.

FIG. 8 illustrates examples of original and obfuscated values, in accordance with an embodiment.

DETAILED DESCRIPTION

Figure 1:
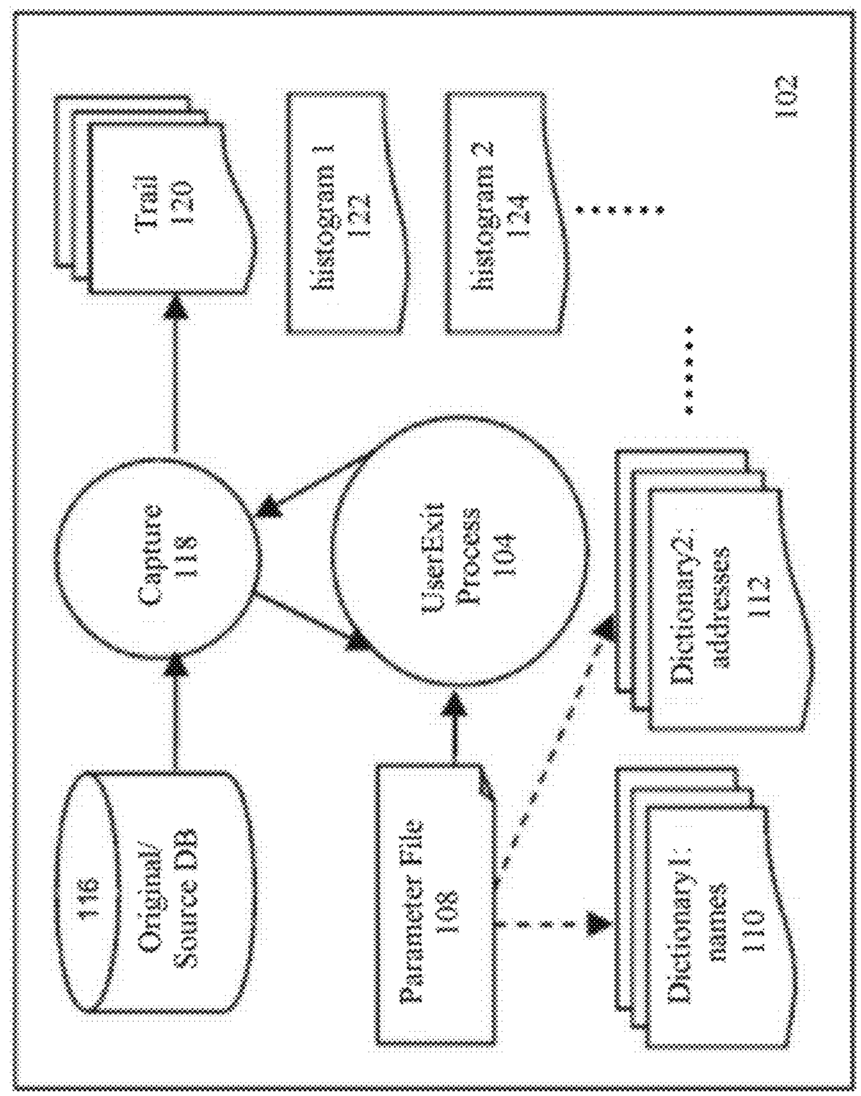
FIG. 1 illustrates an environment or system which can use data obfuscation, in accordance with an embodiment.

Data privacy is no more an optional feature—it is a requirement by any data management system to preserve the privacy of the data of the users of the system. Recently, new privacy laws have appeared, such as the HIPAA laws for protecting medical records, and the PCI guidelines for protecting credit card information. Data privacy (also referred to as information privacy) can be defined as maintaining the privacy of personal identifiable information or data from unauthorized accessing. Data privacy refers to developing relationship and interaction between technology and the privacy of personally identifiable information (PII) that is collected, stored, and shared by organizations. PII includes any piece of data that can be used alone, or in conjunction with additional information, to uniquely identify an individual. Examples of such information may include first and last names, social security numbers, national identification numbers, addresses, date of birth, phone numbers, email addresses, driver's license numbers, credit card numbers, financial, and medical records.

Data security has generally been provided through access control. Although access control methods provide a level of data protection, it is not enough. Access control methods, in addition to data encryption, protect data from unauthorized access. However, it does not prohibit identity thefts. It was recently suggested that that 70% of data privacy breaches are internal breaches that involve an employee from the enterprise who has access to some training or testing database replica, which contains all the PII. Therefore, there is a need for techniques that would prevent such identity thefts. Ideally, what is needed is a technique that would protect the PII from unauthorized access, and allow access for analysis, testing and training purposes, while maintaining its usability. The challenge here is the contradicting requirement of a usable copy of the data that, yet, does not breach the privacy of the data. Examples of systems that can benefit from these requirements may include large financial credit card enterprises.

Data Obfuscation

As referred to herein, Data Obfuscation (DO) is a broad term that refers to any data manipulation technique used to induce ambiguity to the data, desensitize it to be of no sense, yet usable, and thus preserving its privacy. The main requirements of a DO technique are data privacy and usability. Data privacy refers to the fact that the PII are secured and concealed upon applying the DO technique to the data. Usability refers to the fact that the transformed data is still useful and maintains the main statistical and semantic properties of the original data. In addition, there are a set of desired properties, such as:

1. Providing access to the confidential attributes should provide the intruder with no additional information. In other words, the ability to predict the original data given access to the obfuscated data should never be possible to use it to retrieve the original sensitive data given the technique and the obfuscated data.
2. The DO technique should be irreversible. It should never be possible to use it to retrieve the original sensitive data given the technique and the obfuscated data.
3. Semantics and referential integrity must be maintained.
4. Obfuscation must be a repeatable process to guarantee consistency. This means that every time a data item is being obfuscated, it is obfuscated to the same obfuscated data item.

All of these requirements make the task of obfuscating the data efficiently a substantial challenge, which is even more challenging when realtime requirements are added as in the motivating example below.

Consider the case when a software-based data replication product, such as Oracle GoldenGate, is used to replicate bank transactional data across heterogeneous sites, where one copy of the data is replicated to a third party site to be used for real-time analysis purposes, say for fraud detection for instance. One way to do so is to replicate the data, and then apply an existing obfuscation technique in an offline fashion and then use the obfuscated copy for analysis. Note that a mapping between original and obfuscated data items is needed in this example. This can be maintained securely encrypted at the original data host. This solution, although relatively simple, does not satisfy the real-time requirements of the fraud detection. In addition, a copy of the original data is being copied and stored at a third party site before it is being obfuscated, which is a huge security threat. Thus, a need for a real-time transactional data obfuscation technique is needed: a technique that satisfies all desired properties of obfuscation techniques, in addition to satisfying the real-time requirements.

As disclosed herein, in accordance with an embodiment a system and method is disclosed for providing a transactional data obfuscation solution, which can be used, e.g. with software-based data replication products such as Oracle GoldenGate. In accordance with an embodiment, the system utilizes different obfuscation functions for different data types to securely obfuscate, on real-time, the data while maintaining statistical characteristics of the data, for testing and analysis purposes.

Many techniques have been proposed for data privacy such as: (1) data randomization, which adds noise to the data; (2) data anonymization, which uses generalization and suppression to make the data ambiguous; (3) data swapping, which involves ranking data items and swapping records that are close to each other; (4) geometric transformation, which uses transformations such as rotation, scaling, and translation for distorting the data; and (5) nearest neighbor data substitution, which uses Euclidean distance to define neighbors, and then perform swapping. Some of these techniques apply to only certain data types; for example, geometric transformation techniques apply only to numerical data. The majority of these techniques were developed for privacy protection for data mining and analysis, for which there are no real-time requirements. To the inventor's knowledge, all these techniques involve an offline analysis phase, at which the statistical characteristics of the data set is captured, and used to guide the obfuscation, in order to maintain these statistical characteristics.

In some environments, such as with a software-based data replication product such as Oracle GoldenGate, transactional data is being replicated on real-time fashion, and hence, a real-time obfuscation technique is needed. In accordance with an embodiment, the system provides a suite of techniques for obfuscating different data types. For example, for numerical data, a technique is proposed herein that is based on both geometric transformation, namely GT-NeNDS, and anonymization. These two techniques are described in more detail below.

GT-NeNDS is a numerical data obfuscation technique that is designed for clustering mining. In accordance with an embodiment, GT-NeNDS is extended to make it applicable in real-time, by applying anonymization, which adds to the data privacy, and increases reversibility, at the expense of data loss. However, this data loss can be controlled, as explained in further detail below.

Anonymization techniques map multiple data items into one; for example, it can replace the date with the month and year only. This generalization involves a loss of information, but data stays consistent. K-anonymity aims at mapping at maximum k data items into one representing data item. Anonymization techniques are irreversible, since there no way to know the original data item.

GT-NeNDS stands for Geometric Transformation—Nearest Neighbor Data Substitution. GT techniques include scaling, rotating, and translation, these preserve data characteristics. The NeNDS technique was proposed for privacy preservation for Clustering Mining applications. It proceeds like this: it clusters the original dataset into sets of neighbors. Neighborhood is determined using Euclidean Distance. Each data item in a neighbors' set is replaced by the nearest neighbor in this set, in a way such that no swapping occurs, using special data structures. Thus, statistical properties of the original data are preserved. NeNDS introduce a degree of obfuscation by replacing a data item with its nearest neighbor. GT-NeNDS aims at securing the data by further obfuscating the nearest neighbor, using the GT techniques.

GT-NeNDS does not adequately fit real-time requirements due to the following reasons. First, to construct the sets of neighbors, the algorithm needs a pass through all the data, which is not feasible in real-time settings. Second, substituting a data item with its nearest neighbor means that the substitution is not repeatable because neighbors changes with insertions and deletions.

To overcome these shortages, in accordance with an embodiment, a GT-ANeNDS technique, and an extension to GT-NeNDS are disclosed herein.

System Architecture

FIG. 1 illustrates an environment or system which can use data obfuscation, in accordance with an embodiment. As shown in FIG. 1, the system 102 can be implemented with or as part of a software-based data replication product, such as Oracle GoldenGate (and which, in accordance with an embodiment, is referred to herein as BronzeGate). The system includes a userExit process 103, which performs user defined customized transformations to the replicated transactions. The system (i.e. BronzeGate) is hence a special type of userExit process, where the task is to perform the required obfuscation on the fly.

As further shown in FIG. 1, the process can be configured to run at an original database site 116, to obfuscate the transactional data before they are shipped to a replicate site, for example as part of a trail information 120, such as a GoldenGate trail file. The process is activated by the capture process 118, which monitors the original database. Whenever a transaction is committed to the original database, the capture process will capture this change and signals the userExit (BronzeGate) process to handle this transaction. The system then uses the parameters file 108, histograms 122, 124, and dictionaries 110, 112 to obfuscate the new transaction. Once done, the system sends the obfuscated transaction back to the capture process which simply writes it to the trail, which shall be shipped to the replication site.

In accordance with an embodiment a GT-ANeNDS technique is proposed herein, which overcomes GT-NeNDS' real-time limitations, and leverage the level of data privacy.

FIG. 2 illustrates the use of a GT-ANeNDS algorithm 130, in accordance with an embodiment. GT-ANeNDS combines anonymization and NeNDS techniques, which yields to gain efficiency, real-time adherence, repeatable mapping, and higher level of data privacy. This comes at the expense of information loss. However, this loss is controlled so that the data usability is not affected. In accordance with an embodiment, GT-ANeNDS can be applied to any data type for which a distance function can be defined. The higher level view of the algorithm is provided first and explained using numerical data type. In the discussion hereafter, by dataset we refer to a field, or a column, in the original database schema. FIG. 2 lists the main steps of the GT-ANeNDS approach. The input to the algorithm consists of the new transactional data item, and the meta-data. The meta-data consists of data-type, histogram and semantics:

- Data-Type: The data-type is the regular database type, i.e., numerical, text, timestamp, etc. In addition to the semantics, datatype is used to determine the technique to use.
- Histogram: The term histogram is used in a generic way to refer to the data structure that is incrementally maintained.
- Semantics: The semantics of each data set is a record of the following information whenever applicable. Data-Sub-Type: for numerical data, the sub-type defines whether the data are general, or identifiable. Where identifiable data can identify the person, such as the national ID number. Euclidean distance Function: the function to be used to calculate the Euclidean distance between two values. The Origin point: the reference point of this data set.

Given the data-type and the semantics, the appropriate obfuscation technique is determined. In case it is GT-ANeNDS, the origin-point and the Euclidean distance function determine the appropriate bucket in the histogram, and the nearest neighbor therefore. Next, GT function is applied to the nearest neighbor, generating the obfuscated value. Next, we illustrate how the GT-ANeN DS works in case of numerical data types.

Numerical Data

Figure 3:
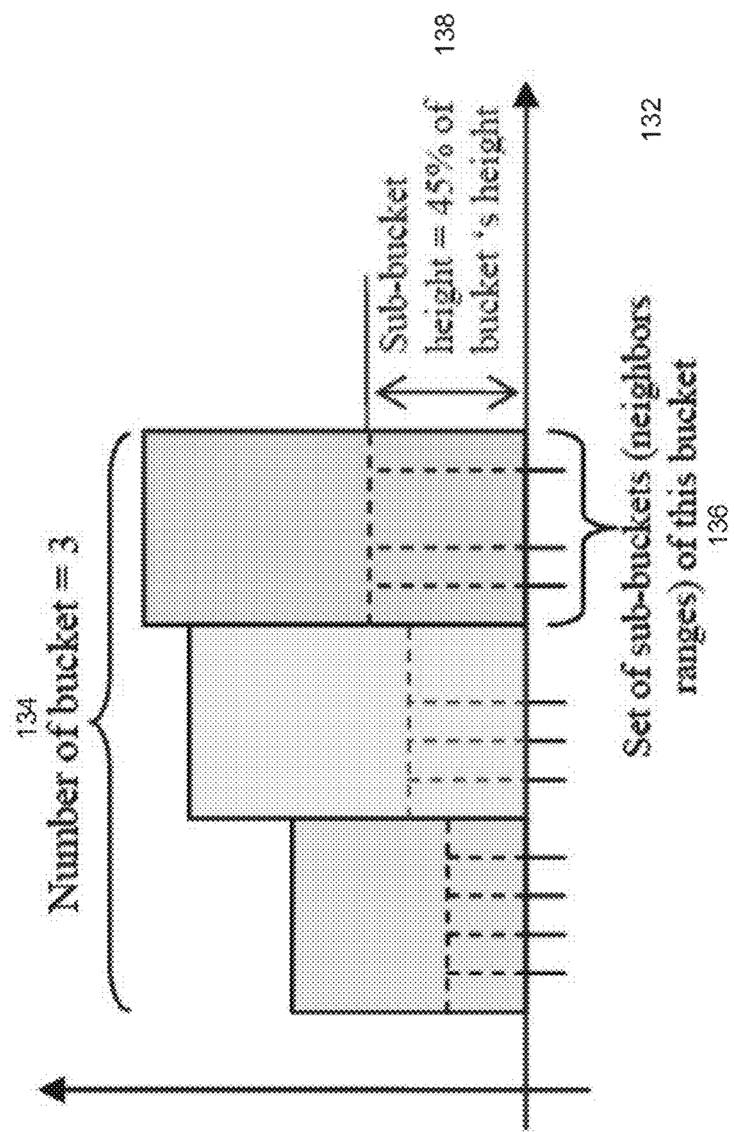
FIG. 3 illustrates histogram decomposition for numerical data, in accordance with an embodiment.

FIG. 3 illustrates histogram decomposition 132 for numerical data, in accordance with an embodiment. For general numerical data (i.e., non ID's such as bank account balance), the system can use equi-width histograms that splits the range of the data items distances into regions of the same width (i.e., range) to define the set of neighbors. Each bucket's 134 range is divided into a set of equi-height sub-buckets 136. The bucket's width and the subbucket's height are systems parameters set by the administrator. Histograms are built by scanning the current database shot once. The number of neighbors for each bucket depends on the height of the bucket 138 and the position of these neighbors depends on the values distribution in this range. Note that the horizontal axis is not the data value; however, it is the distance from the origin point. The vertical access is the frequency. This is introduced to be able to identify the nearest neighbor without the need to maintain any summary about the data values within each bucket.

The GT-ANeNDS process proceeds as follows. First, the distance between the original data item's value and the origin point is calculated, determining where in the histogram this data item falls. Second, the nearest neighbor point in the histogram is determined. The neighbors set, is the set of points determining sub-buckets' ranges within the same bucket this point belongs to. Finally, geometric transformation is applied to the nearest neighbor, generating the obfuscated value. A difference between the GT-NeNDS and GT-ANeNDS processes is that GT-ANeNDS uses a fixed set of neighbors for each bucket, which yields to map more than one original data value to the same obfuscated value, i.e., Anonymization. By fine tuning the bucket widths and the sub-bucket heights, the statistical characteristics of the original data are minimally impacted.

Boolean Data

In accordance with an embodiment, for Boolean datatype, the same approach is used but the process simply uses two buckets only, and no sub-buckets. Therefore, the system can maintain in this case two counters for each bucket. To obfuscate a value, the new value is randomly drawn with probability to have the same ratio of the two values. For example, if it is a Gender field and the counters are: ten females and seven males, then the obfuscated value is set to M (i.e., male) with probability 7/17.

Identifiable Numerical Data

FIG. 4 illustrates a function for obfuscating identifiable numerical data 140, in accordance with an embodiment. For a numerical value is a key, such as national identification number, anonymization is not valid as it will result in distortion of the referential integrity constraints. In accordance with an embodiment, a Special Function 1 illustrated in FIG. 4 can be used. Opposed to NeNDS, the process can use a FaNDS technique (Farthest Neighbor Data Substitution). This is exactly same as NeNDS except that the process substitutes the data item with its farthest neighbor. Each digit of the original value is treated as a separate value to obfuscate. The set of digits are used as the neighbors from which the farthest neighbor is chosen to replace the original digit. Next, rotation is applied for each replaced digit and saved in a temporarily variable. This rotated number that results from replacing each digit in the original key and then rotating it is being added to the original key value and result is truncated to the key length and saved in a second temporarily variable. Finally, the obfuscated key is generated by randomly picking each digit from the two temporarily variables.

Date Data

For date data type, neither GT-ANeNDS nor Special Function 1 fits, because of the semantics of the date. Therefore, in accordance with an embodiment the process can use a Special Function 2, to obfuscated date and timestamp data types, wherein the function basically utilizes controlled randomness to obfuscate each component of the date, i.e., the day, month and year.

Other Data Types

FIG. 5 illustrates a table 144 of possible data-types and semantics, and which technique the system can use to obfuscate each data type, in accordance with an embodiment. In accordance with an embodiment, the system allows the user to overwrite these default selections and to define a user-defined obfuscation function. Depending on the implementation, the metadata about which technique to be used and its parameters can be stored in the original database itself, or in a parameters file.

Analysis

In the following sections, the degree of data privacy, repeatability, and data usability of the proposed obfuscation techniques is analyzed.

Anonymization generally guarantees securing data 100%. Hence, numerical general data obfuscated using the GT-ANeNDS and that obfuscated using a dictionary are guaranteed to secure the privacy. For identifiable numerical data, Special Function 1 obfuscates the data using two different techniques then randomly picks digits from both obfuscated values into one new output value. Without full knowledge of the original data, there is no way to find out from where each digit was picked. Thus, data privacy is maintained, and the proposed obfuscation techniques are immune even to partial attacks, in which partial knowledge about the original data and/or the obfuscation process are used to reverse engineer a portion of the original data.

The proposed techniques guarantee obfuscation repeatability, i.e., applying to the same input data results in the same obfuscated data maintaining referential integrity. In the techniques used, the randomization can be dependant on the original data, i.e. the random seed is generated using the original data value, thus guaranteeing its repeatability.

Data usability is the hardest question to answer for numerical data since the proposed techniques introduce some anonymization. However, since the system determines the number of neighbors and their distances from the origin based on the number and distribution of data values within this bucket, thus the set of neighbors should be representative enough that the anonymized data are still useable.

Performance Issues and Experimental Evaluation

In accordance with an embodiment, initial construction of the histograms and dictionaries is the only offline process within the system. Depending on the application dynamics, this process might need to be repeated, and the database rereplicated. This should be done in an efficient way, minimizing overhead and downtime.

In the following section, some performance results are described to provide a sense of how different techniques perform, and to demonstrate the data usability.

Data Usability

Figure 6:
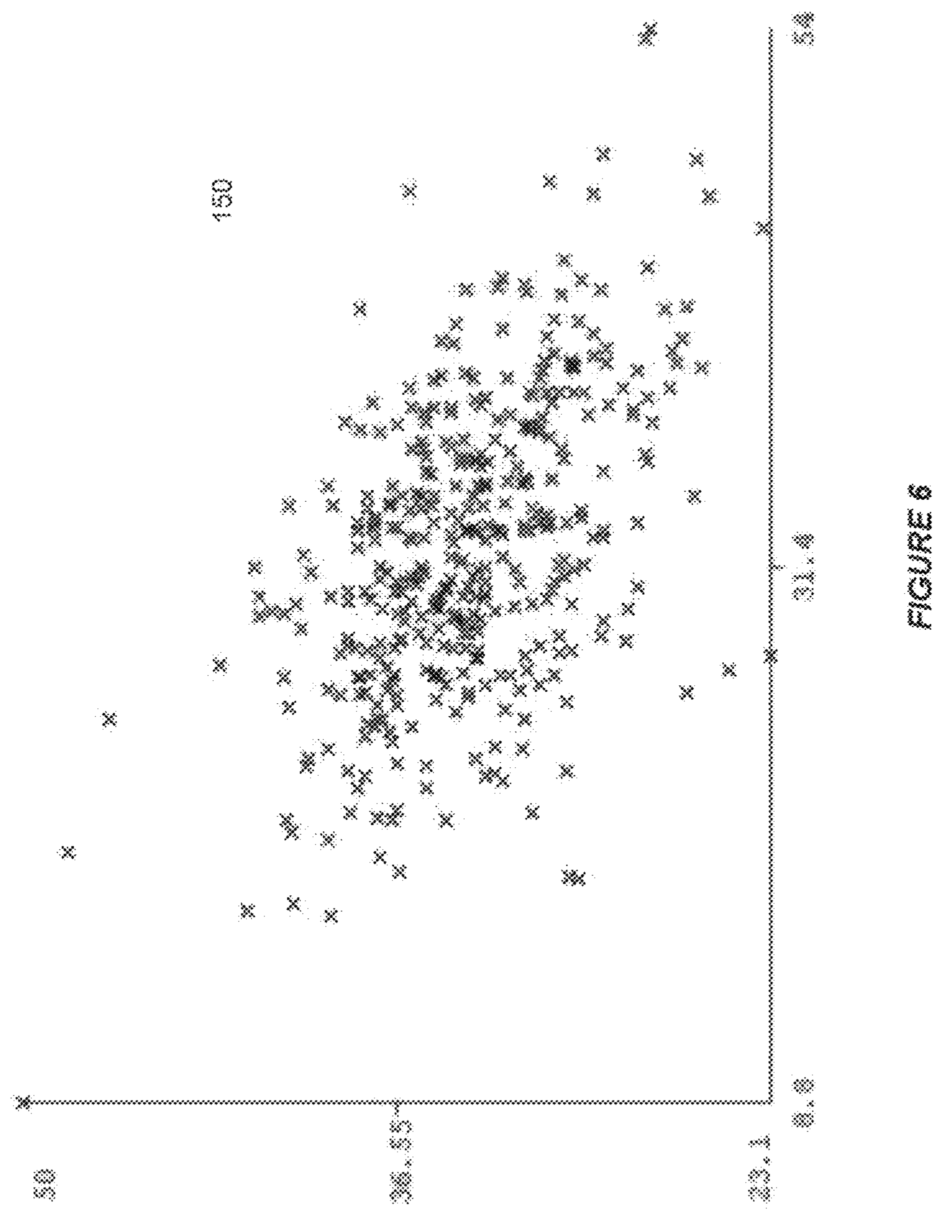
FIG. 6 illustrate the results of the K-mean algorithm on original data, in accordance with an embodiment.
Figure 7:
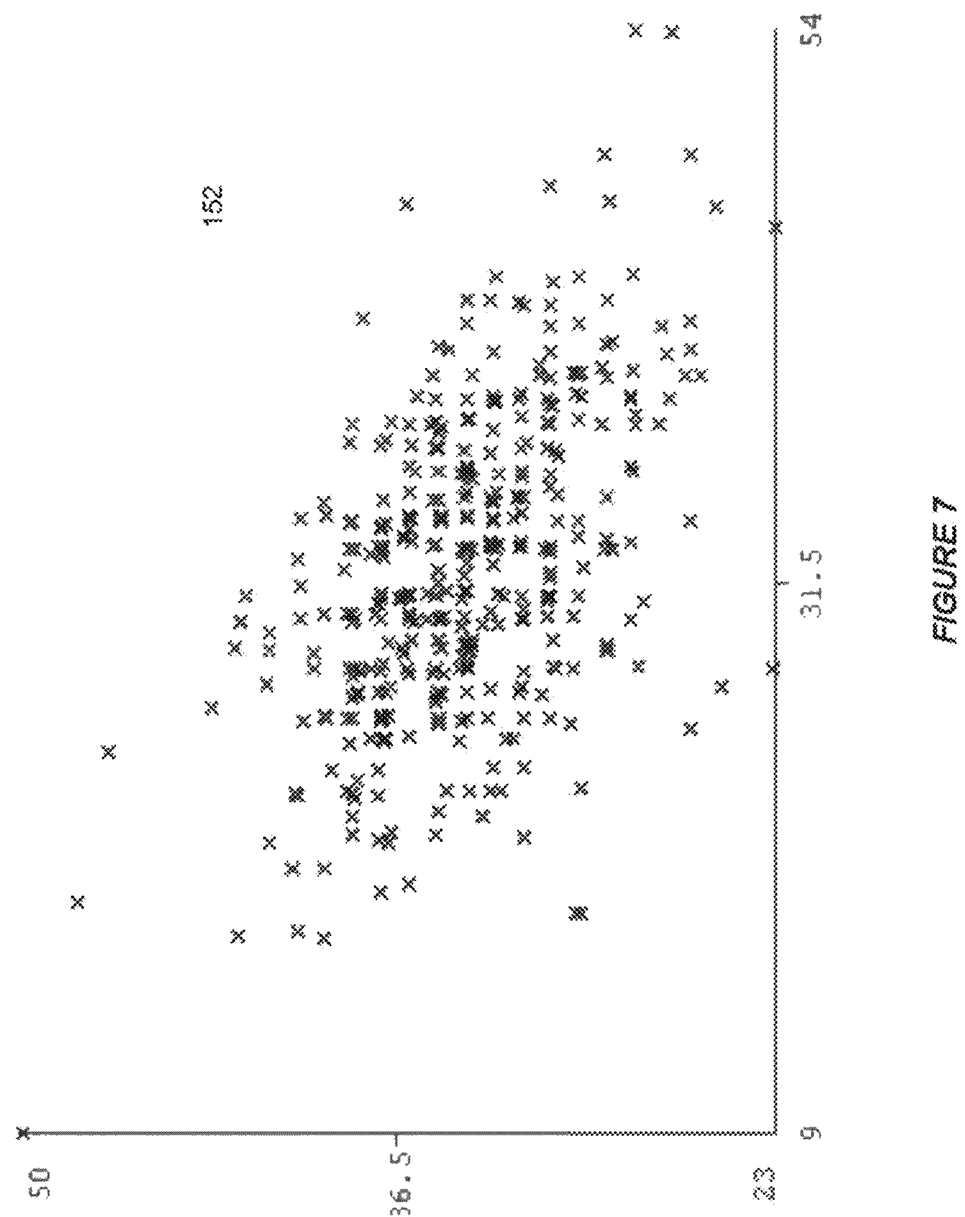
FIG. 7 illustrate the results of the K-mean algorithm on obfuscated data, in accordance with an embodiment.

FIGS. 6 and 7 illustrate the results of the K-mean algorithm on original 150 and obfuscated data 152 respectively, in accordance with an embodiment. In a first experiment, the data usability of the system was demonstrated by applying K-mean classification algorithm, with k=8, using Weka Software to both the original and obfuscated data and plotting the results. The workload is a dataset of protein data in ARFF format. For the data obfuscation, the GT-ANeNDS was applied with theta equal to 45 degrees, origin point was set to the min value found in the original data set, and the histogram parameters were as follows: bucket width equals to one fourth of the range of the original data set, and sub-bucket height was set to 25%, so that there are four subbuckets in each bucket. As can be seen in FIGS. 6 and 7, the classification results are almost exactly the same, which demonstrates the data usability of the process.

Obfuscation Sample Results

FIG. 8 illustrates examples of original and obfuscated values, in accordance with an embodiment. In another experiment, an Oracle database was replicated to an MSSQL one using the system. One table was created that includes all different data types and obfuscated all fields except the notes, to identify the replicated record. The table shows the first five tuples, and their obfuscated replicas. As can be seen from the table, identifiable numerical values (SSN and credit card) are obfuscated using the Special Function 1 into unique (i.e., identifiable) values. The system also updated and deleted tuples as well, and the correct replica reflected the updates, showing the repeatability of the techniques. The table also shows for other data types how obfuscated values secure the original data.

The present invention may be conveniently implemented using one or more conventional general purpose or specialized digital computer, computing device, machine, or microprocessor, including one or more processors, memory and/or computer readable storage media programmed according to the teachings of the present disclosure. Appropriate software coding can readily be prepared by skilled programmers based on the teachings of the present disclosure, as will be apparent to those skilled in the software art.

In some embodiments, the present invention includes a computer program product which is a non-transitory storage medium or computer readable medium (media) having instructions stored thereon/in which can be used to program a computer to perform any of the processes of the present invention. The storage medium can include, but is not limited to, any type of disk including floppy disks, optical discs, DVD, CD-ROMs, microdrive, and magneto-optical disks, ROMs, RAMs, EPROMs, EEPROMs, DRAMs, VRAMs, flash memory devices, magnetic or optical cards, nanosystems (including molecular memory ICs), or any type of media or device suitable for storing instructions and/or data.

The foregoing description of the present invention has been provided for the purposes of illustration and description. It is not intended to be exhaustive or to limit the invention to the precise forms disclosed. Many modifications and variations will be apparent to the practitioner skilled in the art. The embodiments were chosen and described in order to best explain the principles of the invention and its practical application, thereby enabling others skilled in the art to understand the invention for various embodiments and with various modifications that are suited to the particular use contemplated. It is intended that the scope of the invention be defined by the following claims and their equivalence.

What is claimed is:

1. A non-transitory computer-readable storage medium storing instructions which, when executed by a computer, cause the computer to perform operations comprising:

monitoring a database with a capture process;

capturing, via the capture process, a transaction containing data while the transaction is being received and committed at the database;

sending a signal from the capture process to an obfuscation process when the capture process detects that the transaction is being committed;

obfuscating at least some particular data of the data contained in the transaction via the obfuscation process, wherein obfuscating data includes calculating a distance between the particular data and an origin point, determining a nearest neighbor point in a data structure that describes a distribution of data values, applying a geometric transformation to the nearest neighbor point, and generating obfuscated data for said particular data through said applying; and sending the obfuscated data to the capture process.

2. The non-transitory computer-readable storage medium of claim 1, wherein the distribution is incrementally maintained.

3. The non-transitory computer-readable storage medium of claim 1, wherein the operations further comprise:

producing an obfuscated transaction through said calculating, said determining, said applying, and said generating.

4. The non-transitory computer-readable storage medium of claim 1, wherein the operations further comprise:

generating, based on said obfuscated data, an obfuscated transaction using a nearest neighbor data substitution process combined with anonymization.

5. The non-transitory computer-readable storage medium of claim 1, wherein the operations further comprise:

generating an obfuscated transaction based on another transaction that contains data that cannot be determined from the obfuscated transaction.

6. The non-transitory computer-readable storage medium of claim 1, wherein the operations further comprise:

generating an obfuscated transaction based on another transaction; and sending the obfuscated transaction back to a capture process that captured said other transaction.

7. The non-transitory computer-readable storage medium of claim 1, wherein the operations further comprise:

generating a file that reflects an obfuscated transaction generated based on the obfuscated data; and transmitting said file to a target system.

8. The non-transitory computer-readable storage medium of claim 1, wherein the operations further comprise:

generating, based on said obfuscated data, an obfuscated transaction;

transmitting said obfuscated transaction to a target system to replicate, in real-time, changes made to the source database by said transaction.

9. The non-transitory computer-readable storage medium of claim 1, wherein the operations further comprise:

transmitting said obfuscated data to a target system for real-time analysis.

10. The non-transitory computer-readable storage medium of claim 1, wherein the operations further comprise:

sending a signal from the capture process to the obfuscation process in response to the capture process detecting that the transaction is being committed.

11. The non-transitory computer-readable storage medium of claim 1, wherein:

the transaction contains data that is associated with metadata that describes the distribution of data values.

12. The non-transitory computer-readable storage medium of claim 1, wherein the operations further comprise:

capturing, at a source transaction-based system, a first transaction that is designed to replicate, to a target system, in real-time, changes made to data in the source transaction-based system; and sending the obfuscated data within a second transaction to the target system;

wherein the target system is also a transaction-based system.

13. The non-transitory computer-readable storage medium of claim 1, wherein the operations further comprise:

capturing, at a source database, a first transaction that is designed to replicate, to a target database at the target system, in real-time, changes made to data in the source database; and sending the obfuscated data within a second transaction to the target system.

14. The non-transitory computer-readable storage medium of claim 1, wherein the operations further comprise:

configuring an obfuscation process according to one or more parameter files that include dictionary names and histograms; and classifying data based on the histograms.

15. The non-transitory computer-readable storage medium of claim 1, wherein obfuscating data further includes reading a key value that is a set of digits;

storing the set of digits as an original set;

storing the set of digits in a first variable;

for each particular digit in the first variable, performing steps comprising:

selecting, from the set of digits, a farthest neighbor digit that is a farthest neighbor to the particular digit among digits in the set of digits, and replacing the particular digit with the farthest neighbor digit in the first variable;

following performance of said steps, rotating the set of digits within the first variable;

storing, in a second variable, a concatenation of (a) the value of the first variable following said rotating and (b) the original set; and truncating the second variable based on a length of the key value.

16. The non-transitory computer-readable storage medium of claim 15, wherein obfuscating data further includes:

for each position of a digit in the original set of digits, performing steps comprising:

randomly selecting, as a selected digit, either (a) a digit occupying the position in the first variable or (b) a digit occupying the position in the second variable, and placing the selected digit at the position within an obfuscated key value.

17. The non-transitory computer-readable storage medium of claim 1, wherein obfuscating data further includes:

reading a date value comprising a month, day, and year; and generating an obfuscated date value by performing steps comprising:

replacing the month with a random month;

replacing the day with a random day; and replacing the year with a random year.

18. The non-transitory computer-readable storage medium of claim 1, wherein the operations further comprise:

capturing an original transaction that contains the particular data;

producing, based at least in part on said calculating, said determining, said applying, and said generating, an obfuscated transaction corresponding to said original transaction;

wherein the obfuscated transaction produced based at least in part on said calculating, said determining, said applying, and said generating is always the same whenever the obfuscated transaction is produced for the original transaction.

19. A method for providing transactional data privacy while maintaining data usability, the method comprising:

monitoring a database with a capture process;

capturing, via the capture process, a transaction containing data while the transaction is being received and committed at the database;

sending a signal from the capture process to an obfuscation process when the capture process detects that the transaction is being committed;

obfuscating at least some particular data of the data contained in the transaction via the obfuscation process, wherein obfuscating data includes calculating a distance between the particular data and an origin point, determining a nearest neighbor point in a data structure that describes a distribution of data values, applying a geometric transformation to the nearest neighbor point, and generating obfuscated data through said applying; and sending the obfuscated data to the capture process.

20. A system, implemented on a computer comprising one or more processors, for providing transactional data privacy while maintaining data usability, comprising:

a capture process, executing on the one or more processors, that monitors a database and captures a transaction containing data while the transaction is being received and committed at the database;

wherein meta-data associated with the data contained in the transaction includes a data structure describing a distribution of data values that is incrementally maintained;

an obfuscation process that receives a signal from the capture process when the capture process detects that the transaction is being committed and obfuscates at least some particular data of the data contained in the transaction, wherein obfuscating data includes calculating a distance between the particular data and an origin point, determining a nearest neighbor point in the data structure that describes a distribution of data values, applying a geometric transformation to the nearest neighbor point, and generating obfuscated data through said applying, and wherein the obfuscation process sends the obfuscated data to the capture process.

* * * * *

UNITED STATES PATENT AND TRADEMARK OFFICE

CERTIFICATE OF CORRECTION

PATENT NO. : 10,860,732 B2
APPLICATION NO. : 14/925870
DATED : December 8, 2020
INVENTOR(S) : Guirguis et al.

It is certified that error appears in the above-identified patent and that said Letters Patent is hereby corrected as shown below:

On the Title Page

On page 2, Column 2, under Other Publications, Line 29, delete “Internation” and insert -- International --, therefor.

In the Specification

In Column 2, Line 58, delete “that that” and insert -- that --, therefor.

In Column 5, Line 66, delete “GT-ANeN DS” and insert -- GT-ANeNDS --, therefor.

Signed and Sealed this
Twenty-fifth Day of May, 2021

Drew Hirshfeld
*Performing the Functions and Duties of the Under Secretary of Commerce for Intellectual Property and Director of the United States Patent and Trademark Office*